United States Patent
Chrystal et al.

[11] Patent Number: 5,167,696
[45] Date of Patent: Dec. 1, 1992

[54] HERBICIDAL ARYLOXY- AND ARYLAMINO-INDANES

[75] Inventors: Ewan J. T. Chrystal, Wokingham; John E. D. Barton; David Cartwright, both of Reading, all of England

[73] Assignee: Imperial Chemical Industries PLC, London, United Kingdom

[21] Appl. No.: 652,815

[22] Filed: Feb. 7, 1991

[30] Foreign Application Priority Data

Feb. 16, 1990 [GB] United Kingdom ................ 9003551

[51] Int. Cl.$^5$ .................. A01N 37/00; C07C 69/76
[52] U.S. Cl. ........................ 71/106; 71/100; 71/103; 71/105; 71/108; 71/116; 71/118; 71/121; 71/124; 558/62; 558/70; 558/230; 558/389; 558/390; 558/408; 560/65; 562/472; 564/161; 564/265; 564/433
[58] Field of Search ............... 71/124, 108, 116, 121, 71/118, 100, 103, 105, 106; 568/632, 634, 637, 635, 633; 560/65; 562/472; 564/433, 265, 161; 558/389, 390, 408, 62, 70, 230

[56] References Cited

U.S. PATENT DOCUMENTS 4,244,960  1/1981  Schröder et al. ............... 564/99
4,790,870  12/1988  Hunt et al. ..................... 71/94
5,068,394  11/1991  Andree et al. .................. 71/108

FOREIGN PATENT DOCUMENTS 299446  1/1989  European Pat. Off.
368212  10/1989  European Pat. Off.

Primary Examiner—Richard L. Raymond
Assistant Examiner—Shailendra Kumar
Attorney, Agent, or Firm—Joel G. Ackerman

[57] ABSTRACT

A compound of formula (I):

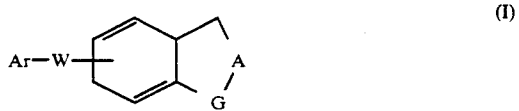

in which Ar is an optionally substituted aryl or heterocyclic ring system;

W is O or $NR^1$ where $R^1$ is hydrogen or lower alkyl;

A is =CH or >$CH_2$ and G is =C—$R^2$, >$CR^3R^4$ or >C=$R^5$ such that —G—A— is —$CR^2$=CH—, where $R^2$ is H or $CR^6R^7XR^8$; or —G—A— is $CR^3R^4$—$CH_2$ where $CR^3R^4$ is CH—$CR^6R^7XR^8$, CH—$OCR^6R^7XR^8$, $C(R^9)OCOR^{10}$, $CR^9R^{10}$, $C(R^9)OR^{10}$, $C(OR^9)OR^{10}$, or CH—$CH_2(CO_2R^{11})$; or —G—A— is —$CR^5$—$CH_2$— where $R^5$ is =$CR^7XR^8$, =$NOCR^6R^7XR^8$, =$NOR^{11}$ or =NO-$COR^{11}$;

X is $(CH_2)_n$, CH=CH, $CH(OR^{20})CH_2$, or $COCH_2$;

n is 0, 1 or 2;

$R^6$ and $R^7$ are independently selected from H, optionally substituted alkyl, alkenyl or alkynyl, halogen, $NR^9R^{10}$, or $R^6$ and $R^7$ together with the carbon to which they are attached form an optionally substituted alkenyl or cycloalkyl group;

$R^8$ is $CO_2R^{12}$, CN, $COR^{12}$, $CH_2OR^{12}$, $CH(OH)R^{12}$, $CH(OR^{12})R^{13}$, $CSNH_2$, $COSR^{12}$, $CSOR^{12}$, $CONHSO_2R^{12}$, $CONR^{14}R^{15}$, $CONHNR^{14}R^{15}$, $CONHN^+R^{14}R^{15}R^{16}R^{17}$, $CO_2^{-+}R^{19+}$ or COON=$CR^{14}R^{15}$;

$R^{19+}$ is an agriculturally acceptable cation;

$R^{17-}$ is an agriculturally acceptable anion;

$R^9$, $R^{10}$, $R^{14}$, $R^{15}$ and $R^{16}$ are independently selected from H or an optionally substituted alkyl, alkenyl, aryl or alkynyl group or any two of $R^9$, $R^{10}$, $R^{14}$ and $R^{15}$, $R^{16}$ together with the atom to which they are attached form a cycloalkyl or heterocyclic ring, and $R^{14}$ and $R^{15}$ may additionally be a heterocyclic ring, provided that when G is $CR^9R^{10}$ or $C(R^9)OR^{10}$, $R^9$ and $R^{10}$ are not both hydrogen.

8 Claims, No Drawings

HERBICIDAL ARYLOXY- AND ARYLAMINO-INDANES

The present invention relates to novel substituted indane derivatives, processes for their preparation, their use as herbicides and herbicidal compositions containing them.

European Patent No 299,446 A describes certain benzheterocyclyl-phenyl ether derivatives which have herbicidal activity. U.S. Pat. No. 4,790,870 describes inter alia aryloxy indane derivatives and their use as herbicides.

According to the present invention there is provided a compound of formula (I):

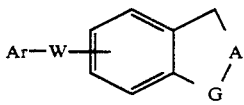

in which

Ar is an optionally substituted aryl or heterocyclic ring system;

W is O or $NR^1$ where $R^{11}$ is hydrogen or lower alkyl;

A is $=CH$ or $>CH_2$ and

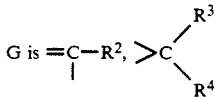

G is $=C-R^2$, $>C<^{R^3}_{R^4}$ or $>C \times 2\ R^5$ such that $-G-A-$ is

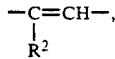

$-C=CH-$, $R^2$ where $R^2$ is H or $CR^6R^7XR^8$; $-G-A-$ is

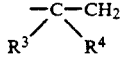

where $CR^3R^4$ is $CH\text{-}CR^6R^7XR^8$, $CH\text{-}OCR^6R^7XR^8$, $C(R^9)OCOR^{10}$, $CR^9R^{10}$, $C(R^9)OR^{10}$, $C(OR^9)OR^{10}$, or $CH\text{-}CH_2(CO_2R^{11})$; or $-G-A-$ is

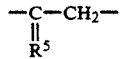

where $R^5$ is $=CR^7XR^8$, $=NOCR^6R^7XR^8$, $=NOR^{11}$ or $=NOCOR^{11}$. where X is $(CH_2)_n$, $CH=CH$, $CH(OR^{20})CH_2$, $COCH_2$; and n is 0, 1 or 2;

$R^6$ and $R^7$ are independently selected from H, optionally substituted alkyl, alkenyl or alkynyl, halogen, $NR^9R^{10}$, or $R^6$ and $R^7$ together with the carbon to which they are attached form an optionally substituted alkenyl or cycloalkyl group;

$R^8$ is $CO_2R^{12}$, CN, $COR^{12}$, $CH_2OR^{12}$, $CH(OH)R^{12}$, $CH(OR^{12})R^{13}$, $CSNH_2$, $CSOR^{12}$, $CSOR^{12}$, $CONHSO_2R^{12}$, $CONR^{14}R^{15}$, $CONHNR^{14}R^{15}$, $CONHN^+R^{14}R^{15}R^{16}R^{17-}$, $CO_2{}^-R^{19+}$ or $COON=CR^{14}R^{15}$;

$R^{19+}$ is an agriculturally acceptable cation;

$R^{17-}$ is an agriculturally acceptable anion;

$R^{11}$, $R^{12}$, $R^{13}$ and $R^{20}$ are independently selected from H or an optionally substituted alkyl, aryl, alkenyl or alkynyl group; and $R^9$, $R^{10}$, $R^{14}$, $R^{15}$ and $R^{16}$ are independently selected from H or an optionally substituted alkyl, alkenyl, aryl or alkynyl group or any two of $R^9$, and $R^{15}$, $R^{16}$ together with the atom to which they are attached form a cycloalkyl or heterocyclic ring, and $R^{14}$ and $R^{15}$ may additionally be heterocyclic rings, provided that when G is $CR^9R^{10}$ or $C(R^9)OR^{10}$, $R^9$ and $R^{10}$ are not both hydrogen.

As used herein the term "alkyl" includes straight or branched chains containing up to 10 carbon atoms preferably from 1 to 6 carbon atoms. The terms "alkenyl" and "alkynyl" refer to unsaturated straight or branched chains having from 2 to 10 and preferably from 2 to 6 carbon atoms. The term "cycloalkyl" includes rings containing from 3 to 9 carbon atoms, preferably from 3 to 6 carbon atoms. The term "alkoxy" includes straight or branched chains containing up to 10 carbon atoms preferably from 1 to 6 carbon atoms.

The term "lower" used in relation to alkyl, alkenyl or alkynyl groups means that the group contains up to 3 carbon atoms.

The term "haloalkyl" and "haloalkoxy" refer to alkyl and alkoxy groups respectively substituted by at least one halogen atom such as fluorine, chlorine or bromine. A particular haloalkyl group is trifluoromethyl. The term "aryl" includes phenyl and naphthyl. The term "heterocyclic" includes rings of up to 10 atoms, preferably up to 6 atoms up to 3 of which are selected from oxygen, nitrogen or sulphur. The term halogen includes fluorine, chlorine, bromine and iodine.

A suitable aryl ring system is phenyl.

Suitable heterocyclic ring systems for Ar, $R^{14}$ or $R^{15}$ are rings of up to 10 atoms, up to 3 of which are selected from oxygen, nitrogen or sulphur, preferably aromatic rings such as pyridine and pyrazole.

Suitable optional substituents for the aryl or heterocyclic ring systems Ar and aryl groups $R^9$, $R^{10}$, $R^{11}$, $R^{12}$, $R^{13}$, $R^{14}$, $R^{15}$, $R^{16}$, $R^{18}$ or $R^{20}$ are up to 5 preferably up to 3 members selected from halogen (fluoro, chloro, bromo or iodo), lower alkyl, haloalkyl (for example $CF_3$), haloalkoxy (for example $OCF_3$), nitro, cyano, lower alkoxy (for example methoxy) or $S(O)_mR^x$ where m is 0, 1 or 2, and $R^x$ is alkyl (for example thiomethyl, sulphinylmethyl and sulphonylmethyl).

Preferred positions of substitution when the aryl ring is a phenyl ring are the 2, 4 and 6 positions, particularly 2,4,6-tri- substituted rings with a trifluoromethyl group at the 4-position.

Examples of optional substituents for alkyl, alkenyl, alkynyl groups $R^6$, $R^7$, $R^9$, $R^{10}$, $R^{11}$, $R^{12}$, $R^{13}$, $R^{14}$, $R^{15}$, $R^{16}$, $R^{18}$ or $R^{20}$ include one or more groups selected from halo such as fluoro, chloro or bromo; nitro; nitrile; aryl such as phenyl; $CO_2R^{21}$, $NHCOR^{21}$ or $NHCH_2CO_2R^{21}$ wherein $R^{21}$ is hydrogen, $C_{1-6}$ alkyl or an agriculturally acceptable cation; $C_{1-6}$ alkoxy; oxo; $S(O)^mR^x$ where $R^x$ and m are as hereinbefore defined (for example thiomethyl, sulphinylmethyl and sulphonylmethyl); amino; mono- or di- $C_{1-6}$ alkylamino; $CONR^{22}R^{23}$ wherein $R^{22}$ and $R^{23}$ are independently selected from hydrogen, $C_{1-6}$ alkyl, $C_{2-6}$ alkenyl or $C_{2-6}$ alkynyl or $R^{22}$ and $R^{23}$ are joined together to form a heterocyclic ring having up to 7 ring atoms 3 of which may be selected from oxygen, nitrogen or sulphur; such as tetrahydrofuranyl.

Examples of agriculturally acceptable cations $R^{19}$ or $R^{21}$ include sodium, potassium or calcium ions, sulphonium or sulphoxonium ions such as $S(O)_p R^{14}R^{15}R^{16}$ where p is 0 or 1, or ammonium or tertiary ammonium ions of formula $N^+R^{14}R^{15}R^{16}R^{18}$ where $R^{14}$, $R^{15}$ and $R^{16}$ are as hereinbefore defined and $R^{18}$ is a further group as hereinbefore defined for $R^{14}$. Suitable substituents for alkyl, alkenyl or alkynyl groups $R^{14}$, $R^{15}$, $R^{16}$ and include hydroxy and aryl. Suitably where any of $R^{14}$, $R^{15}$, $R^{16}$ and $R^{18}$ are optionally substituted alkyl, they contain from 1 to 4 carbon atoms.

Particular examples of $R^{14}$, $R^{15}$, $R^{16}$ and $R^{18}$, in these cations are hydrogen, ethyl, isopropyl, 2-hydroxyethyl and benzyl.

Examples of agriculturally acceptable anions $R^{17-}$ include halide ions such as iodide.

Suitable halo groups $R^6$ and $R^7$ include fluorine, chlorine and bromine.

Suitable heterocyclic rings formed from two of $R^9$, $R^{10}$, $R^{14}$, $R^{15}$, $R^{16}$ or $R^{18}$ and the atom to which they are attached are pyrrolidine, piperidine and morpholine.

Suitably —A—B— is —CH$_2$—CH—CR$^6$R$^7$XR$^8$,
|

—CH=C—CR$^6$R$^7$XR$^8$, —CH$_2$—CH—OCR$^6$R$^7$XR$^8$,
        |                              |

—CH$_2$—C=NOR$^{11}$, —CH$_2$—C=CR$^6$XR$^8$ or
        |                      |

—CH$_2$—C=NOCR$^6$R$^7$XR$^8$.
        |

Preferably $R^6$ is H
Preferably $R^7$ is H or is $C_{1-3}$ alkyl, in particular methyl.

Preferably $R^8$ is $CO_2R^{12}$ or $CONR^{14}R^{15}$.

Preferred examples of $R^{12}$ include $C_{1-6}$ alkyl, optionally substituted by for example lower alkoxy or $C_{2-6}$ alkynyl.

Most preferably $R^{12}$ is $C_{1-6}$ alkyl especially methyl or ethyl.

Preferably $R^{14}$ and $R^{15}$ are independently hydrogen or lower alkyl such as methyl.

Preferably $R^{11}$ is hydrogen.

Preferably —A—B— is or —CH$_2$CH—CR$^6$R$^7$XR$^8$ or —CH$_2$—C=NOCR$^6$R$^7$XR$^8$ where $R^6$ and $R^7$ are hydrogen and $R^8$ is $CO_2R^{12}$ where $R^{12}$ is $C_{1-6}$ alkyl in particular methyl or ethyl.

Preferred groups Ar are groups of sub-formula (i)

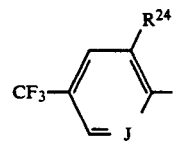

(i)

where $R^{24}$ is hydrogen or halo; and J is N or $CR^{25}$ where $R^{25}$ is hydrogen or halo.

Preferably J is a group $CR^{17}$.

Suitable halo groups for $R^{24}$ and $R^{25}$ are fluorine and chlorine. Most preferably one $R^{24}$ or $R^{25}$ is fluorine and the other is chlorine.

Suitably Ar is optionally substituted phenyl, pyridyl or pyrazolyl, preferably optionally substituted phenyl.

W is preferably oxygen.

Preferably X is $(CH_2)_n$ where n is zero or 1, especially zero.

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Some of the compounds of the invention can exist in enantiomeric forms. The invention includes both individual enantiomers and mixtures of the two in all proportions.

Particular examples of compounds according to the invention are listed in Table I.

TABLE I

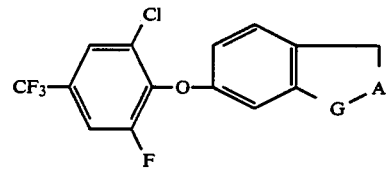

| Compound No. | A—G— | Characterising Data |
|---|---|---|
| 1 | —CH$_2$—CHCH$_2$CO$_2$H (RS form)<br>           | | m.p. 127–128.5° C. |
| 2 | —CH$_2$—CHCH$_2$CO$_2$CH$_3$ (RS form)<br>           | | m.p. 70.5–72° C. |

TABLE I-continued

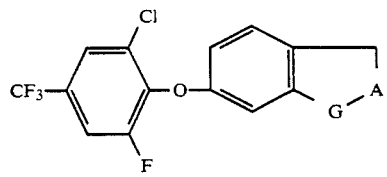

| Compound No. | A—G— | Characterising Data |
|---|---|---|
| 3 | —CH₂  CH—OCH₂CO₂Et (RS form) (with branch) | NMR δH(CDCl₃) 1.25(t)3H; 2.15(m)1H; 2.40(m)1H; 2.80(m)1H; 3.05(m)1H; 4.10(s)2H; 4.20(q)2H; 5.00(m)1H; 6.80(m)1H; 7.00(d)1H; 7.15(d)1H; 7.40(dd)1H; 7.60(broad s)1H. |
| 4 | —CH₂—CH—CH₂CO₂Et (RS form) | NMR δH(CDCl₃) 1.20(t)3H; 1.80(m)1H; 2.40(m)2H; 2.70(dd)1H; 2.90(m)2H; 3.50(m)1H; 4.10(q)2H; 6.70(m)2H; 7.10(d)1H; 7.40(dd)1H; 7.55(broad s)1H. |
| 5 | —CH₂—C=NOH (RS form) | m.p. 170–171° C. |
| 6 | —CH₂—C=CHCO₂Et (Z form) | NMR δH(CDCl₃) 1.20(t)3H; 2.95(s)4H. 4.10(q)2H; 5.95(d)1H; 6.95(dd)1H; 7.25(d)1H; 7.40(dd)1H; 7.60(broad s)1H; 8.40(d)1H. |
| 7 | —CH₂—C=CHCO₂Et (E form) | NMR δH(CDCl₃) 1.30(t)3H; 3.00(m)2H; 3.35(m)2H; 4.10(q)2H; 6.10(t)1H; 7.00(m)2; 7.30(d)1H; 7.40(dd)1H; 7.60(broad s)1H. |
| 8 | —CH=C—CH₂CO₂Et | NMR δH(CDCl₃) 1.20(t)3H; 3.40(d)2H; 3.55(broad s)2H; 6.55(broad s)1H; 6.70(d)1H; 7.35(d)1H; 7.40(dd)1H; 7.60(broad s)1H. |
| 9 | —CH₂—C=NOCH₂CO₂Me | NMR δH(CDCl₃) 3.00(s)4H; 3.75(s)3H; 4.70(s)2H; 7.10(d+dd)2H; 7.25(d)1H; 7.40(dd)1H; 7.60(broad s)1H. |
| 10 | —CH₂—CHCH₂CO₂CH(CH₃)₂ (RS form) | mpt 67–69.5° C. |
| 11 | —CH₂—CHCH₂—CO₂CH₂CH₂OCH₃ (RS form) | NMR δH(CDCl₃) 1.8(m)1H; 2.4(m)2H; 2.8(m)3H; 3.4(s)3H; 3.55(m)3H; 4.2(t)2H; 6.7(m)2H; 7.15(d)1H; 7.4(dd)1H; 7.6(bs)1H. |

TABLE I-continued

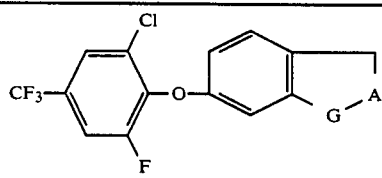

| Compound No. | A—G— | Characterising Data |
|---|---|---|
| 12 | —CH$_2$—CHCH$_2$CO$_2$CH$_2$COCH$_3$ (RS form) | NMR δH(CDCl$_3$) 1.8(m)1H; 2.15(s)3H; 2.5(m)2H; 2.8(m)3H; 3.6(m)1H; 4.65(s)2H; 6.75(m)2H; 7.15(d)1H; 7.4(dd)1H; 7.5(bs)1H. |
| 13 | —CH$_2$—CH—CH$_2$CO$_2$(CH$_2$)$_3$CH$_3$ (RS form) | NMR δH(CDCl$_3$) 0.8(t)3H; 1.35(m)2H; 1.6(m)2H; 1.8(m)1H; 2.4(m)2H; 2.7(dd)1H; 2.8(m)2H; 3.5(q)1H; 4.05(t)2H; 6.7(m)2H; 7.1(d)1H; 7.4(dd)1H; 7.55(s)1H. |
| 14 | CH$_2$—CH—CH$_2$CO$_2$CH$_2$C≡CH (RS form) | NMR δH(CDCl$_3$) 1.8(m)1H; 2.45(m)3H; 2.8(m)3H; 3.55(qn)1H; 4.7(d)2H; 6.7(m)2H; 7.1(d)1H; 7.4(dd)1H; 7.6(bs)1H. |
| 15 | —CH$_2$CH—CH$_2$—CONH$_2$ (RS form) | m.p. 144–149.5° C. |
| 16 | —CH$_2$—CH—CH$_2$CONHCH$_3$ (RS form) | m.p. 154–158.5° C. |
| 17 | —CH$_2$—CH—CH$_2$CON(CH$_3$)$_2$ (RS form) | NMR δH(CDCl$_3$) 1.75(m)1H; 2.45(m)2H; 2.7(dd)1H; 2.85(m)2H; 2.95(s)6H; 3.7(q)1H; 6.65(dd)1H; 6.75(d)1H; 7.1(d)1H; 7.4(dd)1H; 7.55(bs)1H. |

Compounds of formula (I), may be prepared by reacting a compound of formula (II):

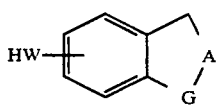

(II)

where W, A and G are is as defined in relation to formula (I) with a compound of formula (III):

Ar—Z   (III)

wherein Ar is as defined in relation to formula (I) and Z is a leaving group, optionally in the presence of a base.

Suitable leaving groups, Z, include halogen, such as fluorine, bromine and chlorine, and sulphonates such as methanesulphonate and p-toluenesulphonate.

Suitable bases for use in the reaction include bases such as sodium hydride, or alkali metal carbonates and hydroxides.

The reaction is preferably carried out in an organic solvent such as dimethylformamide, dimethylsulphoxide, a lower alkanol, or a lower ketone. Moderate temperatures, for example of from 20° to 150° C, are suitably employed. Conveniently the reaction is carried out at 50° C to 120° C.

Compounds of formula (II) and (III) are known compounds or they can be prepared from known compounds by conventional methods.

Alternatively compounds of formula (I) can be prepared by converting a compound of formula (IV):

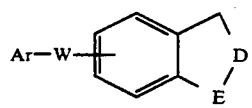

(IV)

where —D—E— is a precursor for groups—A—G— for example-CH$_2$-CHOH or -CH$_2$-C=O, to a compound of formula (I) by reaction with appropriate reagents or series of reagents.

Such reactions and reactants will depend upon the particular groups —A—G— required in the final compound of formula (I) but this can generally be achieved by standard chemical manipulations. For example compounds of formula (I) where —A—G— is

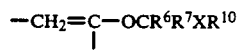

where R$^6$ is hydrogen can be prepared by alkylation of a compound of formula (V):

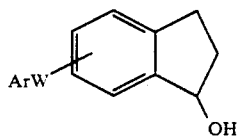

(V)

where Ar and W are as defined in relation to formula (I) with a diazo derivative of formula (VI):

$$N_2CR^7XR^8 \quad (VI)$$

where $R^7$, X and $R^8$ are as defined in relation to formula (I). The reaction is suitably effected in the presence of an appropriate catalyst in an organic solvent such as dimethylsulphoxide, dimethylformamide or tetrahydrofuran. Moderate temperatures for example of from −20° C. to 100° C., preferably 0° C. to 40° C. employed.

An example of a compound of formula (VI) is ethyl diazoacetate. Rhodium II acetate dimer is a suitable catalyst for this procedure.

Compounds of formula (V) can be prepared by reduction of a compound of formula (VII):

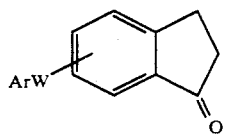

(VII)

using a reducing agent. A suitable reducing agent is sodium borohydride in an organ  solvent such as methanol.

Alternatively the compound of formula (V) can be reacted with a Wittig reagent such as a compound of formula (VIII):

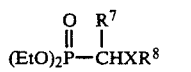

(VIII)

wherein $R^7$, X and $R^8$ are as defined in relation to formula (I). The reaction is suitably effected in an aprotic solvent such as tetrahydrofuran in the presence of a base such as sodium hydride. Moderate temperatures such as −20° C. to 100° C., preferably 0° C. to 50° C. are suitably employed. The product is a mixture of compounds of formula (IA) (both E and Z forms) and (IB):

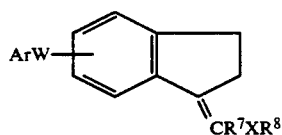

(IA)

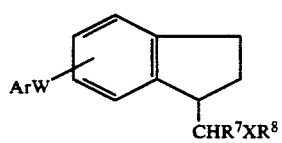

(IB)

This mixture can be separated by chromatography, or reduced to give a compound of formula (IC):

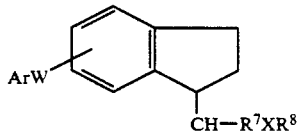

(IC)

The reduction can be effected using palladium on charcoal catalyst at moderate temperatures such as 0° C. to 100° C., for example at room temperature. Suitably the reaction is carried out in a solvent such as toluene or a lower alkanol, for example ethanol.

As another alternative, the compound of formula (VII) is reacted with hydroxylamine hydrochloride in the presence of a base to yield a compound of formula (ID):

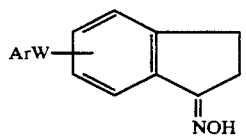

(ID)

The reaction is suitably effected in a solvent such as a mixture of water and a lower alkanol, for example methanol. Moderate temperatures such as 0° C. to 100° C., for example room temperature, are preferably employed Suitable bases include metal hydroxides, carbonates or lower alkanoate, wherein the metal is suitably an alkali metal such as potassium or sodium. A particular example of such a base is for example sodium acetate Compounds of formula (ID) may be reacted with compound of formula (IX) :

$$ZCR^6R^7XR^8 \quad (IX)$$

wherein $R^6$, $R^7$, $R^8$ and X are as defined in relation to formula (I) and Z is a leaving group as hereinbefore defined in the presence of a base to give a compound of formula (IE):

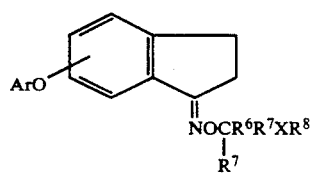

(IE)

The reaction is suitably carried out in a solvent such as tetrahydrofuran, dimethylformamide or dimethylsulphoxide at moderate temperatures such as 20° C. to 110° C., preferably 50° C.-100° C. Suitable bases include alkali metal hydrides, for example sodium hydride.

Compounds (IV), (V), (VI), (VII), (VIII) and (IX) are known compounds or may be prepared by known methods from known compounds.

In particular compounds of formula (VII) may be prepared by reacting compounds of formula (X) :

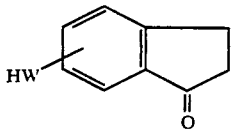 (X)

where W is as defined in relation to formula (I) with a compound of formula (X):

 (IX)

wherein Ar is as defined in relation to formula (I), and Z is a leaving group as hereinbefore defined optionally in the presence of a base.

The reaction is preferably carried out in an organic solvent such as DMF, DMSO, a lower alkanol, or a lower ketone. Higher temperatures, for example from, 50° C. to 200° C., are suitably employed.

Suitable bases for use in the reaction include bases such as sodium hydride, or alkali metal carbonates and hydroxides.

If desired one or more of the following steps may be carried out to convert one compound of formula (I) to another such compound:
  i) when $R^8$ is alkoxycarbonyl hydrolysing to the corresponding acid.
  ii) when $R^8$ is COOH esterifying or forming a salt, amide, sulphonamide, hydrazide or hydrazinium derivative.
  iii) when $R^8$ is an alcohol, oxidation to the corresponding acid or aldehyde.
  iv) when $R^8$ is alkoxycarbonyl, reduction to an alcohol.
  v) when $R^8$ is an amide, dehydration to the corresponding nitrile.

The compounds of formula (I) are active as herbicides and therefore, in a further aspect the invention provides a process for severely damaging or killing unwanted plants which process comprises applying to the plants, or to the growth medium of the plants, an effective amount of a compound of formula (I) as hereinbefore defined The compounds of formula (I) are active against a broad range of weed species including monocotyledenous and dicotyledonous species. They may show some selectivity towards certain species; they may be used as selective herbicides in sugar beet, maize and wheat crops.

The compounds of formula (I) may be applied directly to the plant (post-emergence application) or to the soil before the emergence of the plant (pre-emergence application). They are particularly useful when applied post-emergence.

The compounds of formula (I) may be used on their own to inhibit the growth of, severely damage, or kill plants but are preferably used in the form of a composition comprising a compound of the invention in admixture with a carrier comprising a solid or liquid diluent.

Therefore, in yet a further aspect, the invention provides plant growth inhibiting, plant damaging, or plant killing compositions comprising a compound of formula (I) as hereinbefore defined and an inert carrier or diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic aid. Suitable non-ionic agents are the condensation products of ethylene oxide with fatty alcohols such as oleyl alcohol and cetyl alcohol, or with alkylphenols such as octyl- or nonyl-phenol (e.g. Agral 90) or octylcresol. Other non-ionic agents are the partial esters derived from long chain fatty acids and hexitol anhydrides, for example sorbitan monolaurate; the condensation products of the partial ester with ethylene oxide; and the lecithins; silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogenous for a sufficient time to enable them to be applied by conventional spray equipment. Concentrates conveniently contain 20-90%, preferably 20-70%, by weight of the active ingredient(s). Dilute preparations ready for use may contain varying amounts of the active ingredients(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and suacorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.01 to 20 kilograms per hectare is suitable while from 0.025 to 1 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having complementary action in the particular application.

Examples of useful complementary herbicides include:

A. benzo-2,1,3-thiadiazin-4-one-2,2-dioxides such as bentazone;
B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);
C. 1,3 dimethylpyrazole derivatives such as pyrazoxyfen, pyrazolate and benzofenap;
D. Dinitrophenols and their derivatives (eg. acetates) such as dinoterb, dinoseb and its ester, dinoseb acetate;
E. herbicides such as dinitramine, trifluralin, ethalfluralin, pendimethalin, oryzalin;
F. arylurea herbicides such as diuron, flumeturon, metoxuron, neburon, isoproturon, chlorotoluron, chloroxuron, linuron, monolinuron, chlorobromuron, daimuron, methabenzthiazuron; a
G. phenylcarbamoyloxyphenylcarbamates such as phenmedipham and desmedipham;
H. 2-phenylpyridazin-3-ones such as chloridazon and norflurazon;
I. uracil herbicides such as lenacil, bromacil and terbacil;
J. triazine herbicides such as atrazine, simazine, aziprotryne, cyanazine, prometryn, dimethametryn, simetryne, and terbutryn;
K. phosphorothioate herbicides such as piperophos, bensulide, and butamifos;
L. thiolcarbamate herbicides such as cycloate, vernolate, molinate, thiobencarb, butylate*, EPTC*, tri-allate, di-allate, esprocarb, tiocarbazil, pyridate, and dimepiperate;
M. 1,2,4-triazin-5-one herbicides such as metamitron and metribuzin;
N. benzoic acid herbicides such as 2,3,6-TBA, dicamba and chloramben;
O. anilide herbicides such as pretilachlor, butachlor, alachlor, propachlor, propanil, metazachlor, metolachlor, acetochlor, and dimethachlor;
P. dihalobenzonitrile herbicides such as dichlobenil, bromoxynil and ioxynil;
Q. haloalkanoic herbicides such as dalapon, TCA and salts thereof;
R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;
S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;
T. cyclohexanedione herbicides such as alloxydim and salts thereof, sethoxydim, cycloxyidim, tralkoxydim, and clethodim;
U. sulfonyl urea herbicides such as chlorosulfuron, sulfometuron, metsulfuron and esters thereof; benzsulfuron and esters thereof such as DPX-M6313, chlorimuron and esters such as the ethyl ester thereof, pirimisulfuron and esters such as the methyl ester thereof, 2-[3-(4-methoxy-6-methyl-1,3,5-triazin-zyl)-3-methylureidosulphonyl) benzoic acid esters such as the methyl ester thereof (DPX-LS300) and pyrazosulfuron;
V. imidazolidinone herbicides such as imazaquin, imazamethabenz, imazapyr and isopropylammonium salts thereof, imazethapyr;
W. arylanilide herbicides such as flamprop and esters thereof, benzoylprop-ethyl, diflufenican;
X. amino acid herbicides such as glyphosate and glufosinate and their salts and esters, sulphosate and bialaphos;
Y. organoarsenical herbicides such as monosodium methanearsonate (MSMA);
Z. herbicidal amide derivative such as napropamide, propyzamide, carbetamide, tebutam, bromobutide, isoxaben, naproanilide and naptalam;
AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac dithiopyr and mefanacet;
BB. Examples of useful contact herbicides include: bipyridylium herbicides such as those in which the active entity is paraquat and those in which the active entity is diquat;

*These compounds are preferably employed in combination with a safener such as dichlormid.

EXAMPLE 1

The Example illustrates the preparation of compound 1 in Table 1.

Potasium hydroxide (0.25g) was added to a solution of compound 4 (185g), prepared as described in Example 4 hereafter in a THF/water mixture (4:3, 14ml) and the mixture was heated at reflux for 12 hours, when no starting material remained as determined by tlc.

After cooling, the reaction mixture was diluted with water, washed with diethylether 4 times, acidified with concentrated HCl, and extracted with diethylether (4 times). The combined ether extracts were washed with water, dried over anhydrous sodium sulphate, filtered and concentrated under reduced pressure to give compound 1, (RS)-6-(2-chloro-6-fluoro-4-trifluoromethylphenoxy)indan-1-ylacetic acid, as beige solid (1.6g, 94%), m.p. 127–128.5° C. (hexane).

$\delta_H$(CDCl$_3$) 1.8(m)1H; 2.4(m)2H; 3.55(m)1H; 6.65(dd)1H; 6.75(bs)1H; 7.15(d)1H; 7.44(dd)1H; 7.6(bs)1H.

EXAMPLE 2

This Example illustrates the preparation of Compound No. 2 in Table I.

Dicyclohexylcarbodiimide (DCC) (0.259) was added to a solution cooled by ice containing compound 1 prepared as described in Example 1 (0.4g), methanol, (0.1ml) and dimethylaminopyridine (a catalytic quantity) in dichloromethane (5ml), On warming to room temperature overnight, a white solid precipitated. The solid was filtered off and washed with a small quantity of dichloromethane. The washings and filtrate were combined and concentrated under reduced pressure to give a yellow oil (0.4g). The oil was purified by thin layer preparative chromatography (silica/hexane-diethylether, 7:3) to give compound 2, methyl (RS)-6-(2-chloro-6-fluoro-4-trifluoromethylphenoxy)indan-1-ylacetate as a waxy solid (0.37g, 92%), m.p. 70.5–72° C.

$\delta_H$(CDCl$_3$) 1.8(m)3H; 2.4(m)2H; 2.7(dd)1H; 2.85(m)2H; 3.55(m)1H; 3.65(s)3H; 6.7(m)2H; 7.15(d)H; 7.4(dd)1H; 7.55(bs)1H.

Compound Nos. 10, 11, 12, 13 and 14 were prepared in an similar manner using appropriate reagents and chromatograhic methods.

EXAMPLE 3

This Example describes the preparation of compound 3 in Table I.

STEP A 3-chloro-α,α,α,4,5,-pentafluorotoluene (3.46g) and potassium carbonate (3.6g) were added to a solution of 6-hydroxyindan-1-one (1.95g) in DMSO (30 cm3) and the mixture was heated at 100° C. for 1¼ hours. After cooling to room temperature, the mixture was poured into ice/water and extracted with diethyl ether. The ether extract was dried over anhydrous sodium sulphate, filtered and concentrated under reduced pressure. The residue was purified by column chromatography (silica/hexane-ether-acetic acid, 70:30:5) to give a solid (2.22g), which was dissolved in diethylether, washed with aqueous sodium, bicarbonate, dried over anhydrous sodium sulphate and concentrated under reduced pressure to give 6-(2-chloro-6-fluoro-4-trifluoromethyl-phenoxy)indan-1-one, as an orange/brown solid (1.8g,42%), m.p. 75° C.

$\delta_H$(CDCl$_3$) 2.7(dd)2H; 3.5(dd)2H; 7.0(d)1H; 7.4(d+dd)2H; 7.5(d)1H; 7.6(broad s)1H.

STEP B

Sodium borohydride (0.11 g) was added to a solution of the indanone (Example 3 Step A; 0.5g) in methanol (15 cm$^3$). The mixture was stirred at room temperature for 5 hours and poured into dilute hydrochloric acid. After the addition of aqueous sodium bicarbonate, the aqueous solution was extracted with diethyl ether The ether extract was washed with brine, dried over anhydrous sodium sulphate, filtered and concentrated under reduced pressure. Preparative thin layer chromatography (silica/hexane-ether, 5:5) gave (RS)-6-(2-chloro-6-fluoro-4-trifluoromethylphenoxy)indan-1-ol as a white solid (0.35g,70%), m.p. 101–102° C.

$\delta_H$(CDCl$_3$) 1.8 broad s)1H; 1.9(m)1H; 2.5(m)1H; 2.8(m)1H; 3.0(m)1H; 5.2(broad t)1H; 6.8(m)2H; 7.2(d)1H; 7.4(dd)1H; 7.6(broad s)1H.

STEP C

Rhodium (II) acetate dimer (approximately 10mg) was suspended in a solution of the indanol (Example 3, step B, 0.5g) in dry toluene (10 cm3). A solution of ethyl diazoacetate (0.18g) in a small volume of dry toluene was slowly added dropwise to the reaction mixture. Effervescence was observed, the solid dissolved and the solution turned a blue green colour. The mixture was allowed to stand at room temperature overnight then poured into water. The aqueous mixture was extracted with diethyl ether, washed with brine, dried over anhydrous sodium sulphate, filtered and concentrated under reduced pressure. Preparative thin layer chromatography (silica/hexane-ether, 7:3) gave compound 3, ethyl (RS)-6-(2-chloro-6-fluoro-4-trifluoromethylphenoxy)indan-1-yloxyacetate, as a colourless oil (0.17g,27%).

$\delta_H$(CDCl$_3$) 1.25(t)3H; 2.15(m)1H; 2.40(m)1H; 2.80(m)1H; 3.05(m)1H; 4.10(s)2H; 4.20(q)2H; 5.00(m)1H; 6.80(m)1H; 7.00(d)1H; 7.15(d)1H; 7.40(dd)1H; 7.60(broad s)1H.

EXAMPLE 4

This Example describes the preparation of compound 4 in Table I.

STEP A

Sodium hydride (0.63g of a 65% dispersion in oil) was added to an ice bath cooled solution of triethylphosphonacetate (3.81g) in dry tetrahydrofuran (10 cm$^3$). The ice bath was removed and the mixture stirred at room temperature for 1½hours. A solution of indanone (Example 3, step A 5.0 g) in dry tetrahydrofuran (10 cm$^3$) was added and the mixture stirred at room temperature overnight. The reaction mixture was poured into water and extracted with diethyl ether. The ether extract was washed with brine, dried over sodium sulphate, filtered and concentrated under reduced pressure. Column chromatography (silica 4×30cm/hexane-ether, 9:1) gave a mixture of didehydroindanylacetates (3.52g,57%).

STEP B

Reduction of a sample of the mixture of didehydroindanylaetates (0.48g) from step A was effected by hydrogenation, under a slight positive pressure of hydrogen, in absolute ethanol (50ml) in the presence of a catalytic quantity of 5% palladium on charcoal (approximately 10g). Removal of solid by filtration through hiflow and concentration of the filtrate under reduced pressure gave an oil (0.34g). Purification of the oil by preparative thin layer chromatography (silica/hexane-diethylether, 7:3) gave compound 4, ethyl (RS)-6-(2-chloro-6-fluoro-4-trifluoromethylphenoxyindan-1-ylacetate), as a pale yellow oil (0.33g,68%).

$\delta_H$(CDCl$_3$) 1.20(t)3H; 1.80(m)1H; 2.40(m)2H; 2.70(dd)1H; 2.90(m)2H; 3.50(m)1H; 4.10(q)2H; 6.70(m)2H; 7.10(d)1H; 7.40(dd)1H; 7.55(broad s)1H.

EXAMPLE 5

This Example describes the preparation of compound 8 in Table I.

A mixture of didehydroindanylacetates (6.26g) was prepared as described in Example 4 and purified by column chromatography (silica 4.5x30cm/hexane-diethylether, 9:1) to give compound 8, ethyl 5-(2-chloro-6-fluoro-4-trifluoromethylphenoxy)inden-3-ylacetate, as an orange oil (0.1g).

$\delta_H$(CDCl3) 1.2(t)3H; 3.4(d)2H; 3.55(broad s)2H; 6.55(broad s)1H; 6.7(d)1H; 7.35(d)1H; 7.4(dd)1H; 7.6(broad s)1H.

EXAMPLE 6

This Example describes the preparation of compound 6 in Table I.

Compound 6, ethyl (Z)-6-(2-chloro-6-fluoro-4-trifluoromethylphenoxy)indan-1-ylidene-acetate (0.11g), as an orange oil, was obtained as described in Example 5 by column chromatography of the crude mixture of didehydroindanyl acetates.

$\delta_H$(CDCl$_3$) 1.20(t)3H; 2.95(s)4H; 4.10(q)2H; 5.95(d)1H; 6.95(dd)1H; 7.25(d)1H; 7.4(dd)1H; 7.6(broad s)1H; 8.4(d)1H.

On prolonged standing in solution the (Z) isomer converts to the (E) isomer (Example 7).

EXAMPLE 7

This Example describes the preparation of compound 7 in Table I.

Compound 7, ethyl (E)-6-(2-chloro-6-fluoro-4-trifluoromethylphenoxy)indan-1-ylideneacetate (0.85g), as an orange oil, was obtained as described for its isomer, Example 5, by column chromatography of the crude mixture of didehydroindanyl acetates.

$\delta_H$(CDCl$_3$) 1.3(t)3H; 3.0(m)2H; 3.35(m)2H; 4.1(q)2H; 6.1(t)1H; 7.0(m)2H; 7.3(d)1H; 7.4(dd)1H; 7.6(broad s)1H.

EXAMPLE 8

This Example describes the preparation of compound 5 in Table I.

The indanone from (Example 3 step A, 1.0g) was added to a colourless solution of sodium acetate (0.43g) and hydroxylamine hydrochloride (0.22g) in a mixture of water (10 cm$^3$) and methanol (10 cm$^3$) and dissolved on warming. After standing for 2 hours at room temperature, the mixture was heated at reflux for 4½ hours and then allowed to stand at room temperature overnight. The mixture was poured into water and a white precipitate filtered off. After drying, preparative thin layer chromatography of the precipitate (silica/hexane-diethylether, 7:3) gave compound 5, 6-(2-chloro-6-fluoro-4-trifluoromethylphenoxy)indan-1-one 1-oxime, as a white solid (0.49g,43%), m.p. 170–171° C.

δH(CDCl$_3$) 2.9–3.1(m)4H; 7.0(dd)1H; 7.1(d)1H; 7.3(d)1H; 7.4(dd)1H; 7.6(broad s)1H; 8.3(broad s)1H.

EXAMPLE 9

This Example describes the preparation of compound 9 in Table I.

The indanone oxime (Example 8, 1.0g) and methyl bromoacetate (0.48g) were added to a stirred suspension of sodium hydride (0.12g of a 60% oil dispersion) in dry tetrahydrofuran at room temperature. After 6 hours no reaction was observed and a catalytic amount of benzyl triethyl ammonium chloride was added. After leaving over night at room temperature, the reaction mixture was heated at reflux for 12½ hours and followed by glc. After cooling to room temperature, the reaction mixture was poured into water and extracted with diethyl ether. The ether extract was washed with brine, dried over anhydrous sodium sulphate, filtered and concentrated under reduced pressure. Preparative thin layer chromatography (silica/hexane-diethylether, 8:2, two elutions) gave compound 9, methyl 0-[6-(2-chloro-6-fluoro-4-trifluoromethylphenoxy)indan-1-ylideneamino]glycolate as a very pale yellow oil (0.64g,53%), which slowly crystallized on prolonged standing.

$\delta_H$(CDCl$_3$) 3.0(s)4H; 3.75(s)3H; 4.7(s)2H; 7.1(d+dd)2H; 7.25(d)1H; 7.4(dd)1H; 7.6(broad s)1H.

EXAMPLE 10

This example describes the preparation of Compound No. 15 in Table I.

STEP A

A solution of Compound No. 1 (0.25g) in thionyl chloride (10 mls) was warmed briefly with a hot air blower, allowed to cool to room temperature and stirred for one hour. Excess thionyl chloride was evaporated under reduced pressure to give crude RS-6-(2-chloro-6-fluoro-4-trifluoromethyl phenoxy)indan-1-ylacetyl chloride as a green/yellow gum, which was used in Step B without further purification.

STEP B

Aqueous ammonium hydroxide was added to the acetyl chloride (Example 10 Step A) giving a milky precipitate which coagulated to a cream solid on stirring at room temperature for 2 hours. After standing overnight, the mixture was diluted with water and extracted with diethyl ether. The ether extracts were dried over anhydrous sodium sulphate, filtered and concentrated under reduced pressure to give Compound No. 15, (RS)-6-(2-chloro-6-fluoro-4-trifluoromethylphenoxy)-indan-1-ylacetamide, as a white solid (0.15g, 60%) m.p. 144–149.5° C.

EXAMPLE 12

This example describes the preparation of Compound No. 16 in Table I.

Dicyclohexylcarbodiimide (DCC) (0.145g) was added to a solution of Compound No. 1 (0.25g) triethylamine (0.134ml), dimethylaminopyridine (a catalytic quantity) and methylamine hydrochloride (0.065g) in dichloromethane (15mls), which was cooled by an ice bath.

On warming to room temperature and stirring for 3 days a white solid precipitated. The solid was filtered off and washed with a small qauntity of dichloromethane/hexane, 1:1.

The washings and filtrate were combined and concentrated under reduced pressure to give a white solid (0.37g). The solid was purified by thin layer preparative chromatography (silica/hexane-ethylacetate, 2:1, 2 elutions) to give Compound No. 16, N-methyl-(RS)-6-(20chloro-6-fluoro-4-trifluoromethylphenoxy)indan-1-yl acetamide, as a white solid (0.15g, 58%) m.p 154–158.5° C. Compound No. 17 was prepared in a similar manner using appropriate reagents.

BIOLOGICAL DATA

The herbicidal activity of the compounds was tested as follows:

Each compound in the appropriate concentration was incorporated into a 4% emulsion of methylcyclohexanone and 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monolaurate. Formulation was effected by dissolving the compound in the requisite amount of solvent/sufactant blend. If necessary, glass beads were added, the total liquid volume adjusted to 5ml with water, and the mixture shaken to effect complete dissolution of the compound. The formulation so prepared, after removal of beads where necessary, was then diluted to final spray volume (45ml) with water.

The spray compositions so prepared were sprayed onto young pot plants (post-emergence test) at a rate equivalent to 1000 litres per hectare. Damage to plants was assessed 13 days aftr spraying by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damae, 6 is 60–69% damage, 7 is 70–79% damage, 8 is 80–89% damage and 9 is 90–100% damage.

In a test carried out to detect pre-emergence herbicidal activity, crop seeds were sown at 2cm depth (i.e. Sb, Ct, Rp, Ww, Mz, Rc, Sy) and weed seeds at 1 cm depth beneath compost and sprayed with the compositions at the rate of 1000 litres per hectare. 20 days after spraying, the seedlings in the sprayed plastic trays were compared with seedlings in unsprayed control trays, the damage being assessed on the same scale of 0 to 9.

The results of the tests are given in Table II below.

TABLE II

| COMPOUND NO. | RATE OF APPLICATION | PRE- OR POST-EMERGENCE APPLICATION | TEST PLANTS (see Table III) | | | | | | | | | | | | |
|---|---|---|---|---|---|---|---|---|---|---|---|---|---|---|---|
| | | | Sb | Rp | Ct | Sy | Mz | Rc | Ww | Pi | Ca | Ga | Am | Bd | Eh |
| 1 | 1 | Pre | 0 | 0 | 0 | 0 | 0 | 0 | 2 | 0 | 5 | — | 7 | 4 | 5 |
| | 0.25 | Post | 4 | 9 | 9 | 9 | 5 | 1 | 0 | 9 | 9 | — | 9 | 3 | 8 |
| 2 | 1 | Pre | 0 | 8 | 0 | 0 | 0 | 0 | 0 | 9 | 9 | — | 9 | 0 | 0 |
| | 0.25 | Post | 3 | 9 | 9 | 6 | 5 | 2 | 1 | 9 | 9 | — | 9 | 5 | 9 |
| 3 | 1 | Pre | — | 0 | 3 | 0 | 0 | 2 | 0 | 5 | 7 | 0 | 8 | 0 | 4 |
| | | Post | 8 | 9 | 9 | 9 | 7 | 3 | 5 | 9 | 9 | 9 | 9 | 9 | 9 |
| 4 | 1 | Pre | 0 | 7 | 4 | 3 | 0 | 0 | 0 | 3 | 6 | 3 | 9 | 3 | 3 |
| | | Post | 5 | 9 | 9 | 9 | 9 | 6 | 5 | — | 9 | 9 | 9 | 8 | 8 |
| 5 | 1 | Pre | 2 | 1 | 0 | 0 | 0 | 6 | 0 | 2 | 6 | 2 | 7 | 0 | 3 |
| | 0.25 | Post | 7 | 8 | 9 | 5 | 8 | 1 | 2 | 5 | 9 | 9 | 9 | 5 | 9 |
| 6 | 1 | Pre | 0 | 0 | 0 | 0 | 0 | 3 | 0 | 3 | 9 | 0 | 9 | 0 | 0 |
| | 0.25 | Post | 4 | 9 | 9 | 6 | 6 | 2 | 2 | 3 | 9 | 6 | 9 | 5 | 8 |
| 7 | 1 | Pre | 0 | 2 | 2 | 0 | 0 | 5 | 2 | 5 | 9 | 3 | 9 | 0 | 0 |
| | 0.25 | Post | 5 | 9 | 8 | 5 | 6 | 2 | 3 | 2 | 9 | 6 | 9 | 3 | 7 |
| 8 | 1 | Pre | 0 | 0 | 0 | 0 | 0 | 0 | 0 | 6 | 9 | 2 | 9 | 0 | 0 |
| | 0.25 | Post | 5 | 8 | 9 | 6 | 6 | 3 | 2 | 4 | 9 | 8 | 9 | 5 | 8 |
| 9 | 1 | Pre | 8 | 7 | 0 | — | 0 | 3 | 4 | 8 | 9 | 5 | 9 | 4 | 8 |
| | | Post | 9 | 9 | 9 | 9 | 9 | — | 7 | — | 9 | 9 | 9 | 9 | 9 |
| 10 | 1 | Pre | 0 | 0 | 0 | 0 | 0 | 0 | 0 | 0 | 9 | — | 9 | 0 | 9 |
| | 0.25 | Post | 4 | 6 | 1 | 3 | 5 | 0 | 0 | 7 | 8 | — | 9 | 3 | 8 |
| 11 | 1 | Pre | 0 | 0 | 5 | 4 | 3 | 3 | 2 | 7 | 7 | — | 9 | 0 | 7 |
| | 0.25 | Post | 5 | 9 | 9 | 5 | 2 | 2 | 2 | 9 | 9 | 9 | 9 | 3 | 9 |
| 12 | 1 | Pre | 0 | 2 | 0 | 0 | 1 | 5 | 0 | — | 9 | — | 9 | 0 | 1 |
| | 0.25 | Post | 5 | 9 | 9 | 6 | 6 | 2 | 0 | — | 0 | — | 9 | 3 | 9 |
| 13 | 1 | Pre | 4 | 8 | 0 | 0 | 3 | 0 | 0 | — | 9 | — | 9 | 2 | 4 |
| | 0.25 | Post | 5 | — | 9 | 8 | 3 | 2 | 3 | 9 | 6 | 9 | 9 | 5 | 7 |
| 14 | 1 | Pre | 0 | 0 | 0 | 0 | 0 | 0 | 0 | — | 9 | — | 9 | 2 | 6 |
| | 0.25 | Post | 6 | — | 9 | 8 | 5 | 0 | 3 | 9 | 9 | 9 | 9 | 5 | 9 |
| 15 | 1 | Pre | 4 | 3 | 0 | 0 | 0 | 0 | 5 | — | 9 | — | 9 | 3 | 5 |
| | 0.25 | Post | 8 | 9 | 8 | 5 | 9 | 4 | 2 | 8 | 9 | 8 | 9 | 6 | 8 |
| 16 | 1 | Pre | 2 | 0 | 0 | 5 | 0 | 0 | 0 | — | 9 | 0 | 9 | 5 | 9 |
| | 0.25 | Post | 8 | 6 | 9 | 5 | 8 | 3 | 2 | 9 | 8 | 9 | 9 | 5 | 9 |
| 17 | 1 | Pre | 2 | 0 | 0 | 0 | 0 | 0 | 0 | — | 9 | 0 | 9 | 4 | 7 |
| | 0.25 | Post | 7 | 4 | 9 | 6 | 7 | 2 | 3 | 9 | 7 | 4 | 9 | 5 | 8 |

| COMPOUND NO. | RATE OF APPLICATION | PRE- OR POST-EMERGENCE APPLICATION | TEST PLANTS (see Table III) | | | | | | | | | | | |
|---|---|---|---|---|---|---|---|---|---|---|---|---|---|---|
| | | | Ip | Ab | Xa | Xs | Av | Al | Ag | Sh | St | Dg | Ec | Ce |
| 1 | 1 | Pre | 0 | 3 | 0 | — | 1 | 2 | — | 0 | 0 | 7 | 0 | 0 |
| | 0.25 | Post | 8 | 8 | — | 5 | 4 | 1 | — | 4 | 5 | 0 | 0 | 0 |
| 2 | 1 | Pre | 0 | 9 | 0 | — | 1 | 2 | — | 0 | 5 | 7 | 0 | 0 |
| | 0.25 | Post | 9 | 9 | — | 5 | 2 | 1 | — | 7 | 9 | 7 | 0 | 1 |
| 3 | 1 | Pre | 0 | 5 | 0 | — | 0 | 0 | — | 0 | 0 | — | 0 | 3 |
| | | Post | 9 | 9 | — | 9 | 5 | 6 | 6 | 9 | 9 | 9 | 9 | 3 |
| 4 | 1 | Pre | 0 | 5 | 0 | — | 0 | 4 | — | 0 | 6 | — | 3 | — |
| | | Post | 9 | 9 | — | 7 | 5 | 6 | 6 | 9 | 9 | 9 | 9 | — |
| 5 | 1 | Pre | 5 | 2 | 0 | — | 0 | 0 | — | 0 | 5 | 6 | 0 | — |
| | 0.25 | Post | 6 | 8 | — | 5 | 2 | 2 | 3 | 5 | 5 | 7 | 7 | — |
| 6 | 1 | Pre | 0 | 9 | 0 | — | 0 | 0 | — | 0 | 7 | 2 | 0 | — |
| | 0.25 | Post | 4 | 8 | — | 3 | 3 | 2 | 3 | 5 | 4 | 5 | 4 | — |
| 7 | 1 | Pre | 0 | 9 | 0 | — | 0 | 0 | — | 0 | 7 | 4 | 0 | — |

TABLE II-continued

|  |  |  |  |  |  |  |  |  |  |  |  |  |  |
|---|---|---|---|---|---|---|---|---|---|---|---|---|---|
|  | 0.25 | Post | 9 | 8 | — | 3 | 3 | 2 | 5 | 7 | 4 | 7 | 5 | — |
| 8 | 1 | Pre | 0 | 8 | 0 | — | 0 | 0 | — | 0 | 0 | 0 | 0 | — |
|  | 0.25 | Post | 8 | 9 | — | 5 | 5 | 2 | 4 | 9 | 6 | 7 | 7 | — |
| 9 | 1 | Pre | 5 | 6 | 5 | — | 6 | 0 | — | 9 | 7 | 9 | 0 | — |
|  |  | Post | 9 | 9 | — | 9 | 7 | 7 | 9 | 9 | 9 | 9 | 9 | 3 |
| 10 | 1 | Pre | 0 | 0 | 0 | — | 0 | 2 | — | 0 | 0 | 5 | 0 | 0 |
|  | 0.25 | Post | 0 | 4 | — | 4 | 0 | 1 | — | 9 | 4 | 0 | 0 | 0 |
| 11 | 1 | Pre | 2 | 3 | 0 | — | 0 | 0 | — | 4 | 5 | — | 0 | 0 |
|  | 0.25 | Post | 6 | 9 | 0 | 2 | 2 | 0 | 5 | 2 | 0 | 2 | 0 | 0 |
| 12 | 1 | Pre | 0 | 5 | 0 | — | 4 | 0 | — | 0 | 4 | — | 0 | 0 |
|  | 0.25 | Post | 9 | 9 | — | 5 | 2 | 1 | 0 | 0 | 5 | — | 0 | 1 |
| 13 | 1 | Pre | — | 5 | 0 | — | 0 | 0 | — | 0 | 0 | — | 0 | 0 |
|  | 0.25 | Post | 7 | 9 | — | 5 | 3 | 3 | — | 5 | 8 | 7 | 6 | 2 |
| 14 | 1 | Pre | — | 8 | 0 | — | 0 | 0 | — | 0 | 0 | — | 0 | 0 |
|  | 0.25 | Post | 9 | 9 | — | 6 | 3 | 5 | — | 5 | 7 | 7 | 6 | 3 |
| 15 | 1 | Pre | 0 | 6 | 0 | — | 0 | 0 | — | 0 | 4 | — | 0 | 0 |
|  | 0.25 | Post | 9 | 9 | — | 6 | 5 | 4 | 4 | 6 | 5 | 9 | 3 | 4 |
| 16 | 1 | Pre | 0 | 8 | 0 | — | 0 | 0 | — | 0 | 9 | — | 0 | 0 |
|  | 0.25 | Post | 7 | 7 | — | 5 | 2 | 1 | 2 | 9 | 6 | 9 | 5 | 3 |
| 17 | 1 | Pre | 0 | 5 | 0 | — | 0 | 0 | — | 3 | 8 | — | 0 | 6 |
|  | 0.25 | Post | 8 | 9 | — | 5 | 3 | 2 | 2 | 9 | 9 | 9 | 5 | 2 |

TABLE III

Test Plants

| | |
|---|---|
| Sb | Sugar beet |
| Rp | Rape |
| Ct | Cotton |
| Sy | Soybean |
| Mz | Maize |
| Ww | Winter wheat |
| Rc | Rice |
| Bd | *Bidens pilosa* |
| Ip | *Ipomoea lacunosa* (pre-emergence) |
|  | *Ipomoea hederacea* (post-emergence) |
| Am | *Amaranthus retroflexus* |
| Pi | *Polygonum aviculare* |
| Ca | *Chenopodium album* |
| Ga | *Galium aparine* |
| Xa | *Xanthium spinosum* |
| Xs | *Xanthium strumarium* |
| Ab | *Abutilon theophrasti* |
| Eh | *Euphorbia heterophylla* |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Ce | *Cyperus esculentes* |

We claim:

1. A compound of formula (I):

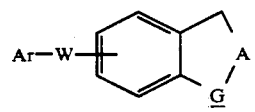

(I)

in which
Ar is optionally substituted phenyl;
W is O or $NR^1$ where $R^1$ is hydrogen or $C_1$-$C_3$ alkyl;
A is =CH or >$CH_2$ and G is =C—$R^2$,

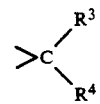

or >C=$R^5$ such that —G—A— is

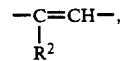

where $R^2$ is H or $CR^6R^7XR^8$, or —G—A— is

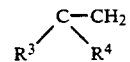

where $CR^3R^4$ is CH-$CR^6R^7XR^8$, CH—$OCR^6R^7XR^8$, $C(R^9)OCOR^{10}$, $CR^9R^{10}$, $C(R^9H)OR^{10}$, $C(OR^9)OR^{10}$, or CH—$CH_2$-($CO_2R^{11}$); or —G—A— is

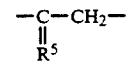

where $R^5$ is $CR^7XR^8$, $NOCR^6R^7R^8$, $NOR^{11}$ or $NOCOR^{11}$, where X is $(CH_2)_n$, CH=CH, $CH(OR^{20})CH_2$, $COCH_2$; and n is 0, 1 or 2;

$R^6$ and $R^7$ are independently selected from H, optionally substituted $C_1$-$C_{10}$ alkyl, $C_2$-$C_{10}$ alkenyl or $C_2$-$C_{10}$ alkynyl, halogen, $NR^9R^{10}$, or $R^6$ and $R^7$ together with the carbonto whcih they are attached from an optionally substituted $C_2$-$C_{10}$ alkenyl or $C_3$-$C_9$ cycloalkyl group;

$R^8$ is $CO_2R^{12}$, CN, $COR^{12}$, $CH_2OR^{12}$, $CH(OH)R^{12}$, $CH(OR^{12})R^{13}$, $CSNH_2$, $COSR^{12}$, $CSOR^{12}$, $CONHSO_2R^{12}$, $CONR^{14}R^{15}$, $CONHNR^{14}R^{15}$, $CONHN^+R^{14}R^{15/}$ $R^{16}R^{17\text{-}}$, $CO_2^-R^{19+}$ or $COON=C^{14}R^{15}$;

$R^{19+}$ is an agriculturally acceptable cation;

$R^{17\text{-}}$ is a halide ion;

$R^{11}$, $R^{12}$, $R^{13}$ and $R^{20}$ are independently selected from H or an optionally substituted $C_1$-$C_{10}$ alkyl, phenyl, $C_2$-$C_{10}$, alkenyl or $C_2$-$C_{10}$ alkynyl gorup;

$R^2$, $R^{10}$, $R^{14}$, $R^{15}$ and $R^{16}$ are independently selected from H or an optionally substituted $C_1$-$C_{10}$ alyl, $C_2$-$C_{10}$ alkenyl, phenyl or $C_2$-$C_{10}$ alkynyl group or any two of $R^9$, $R^{10}$, $R^{14}$ and $R^{15}$, $R^{16}$ together with the atom to whcih they are attached form a $C_3$-$C_9$ cycloalkyl ring; provided that when G is $CR^9R^{10}$ or $C(R^9)OR^{10}$, $R^9$ and $R^{10}$ are not both hydrogen, wherein:

(i) optional substituents for aryl groups comprise up to 3 members selected from halogen, $C_1$-$C_3$ alkyl, $C_1$-$C_6$ haloalkyl, $C_1$-$C_6$ haloalkoxy, nitro, cyano, $C_1$-$C_3$ alkoxy, or $S(O)_mR^x$ in which m is 0, 1 or 2 and $R^x$ is $C_1$-$C_6$ alkyl;

(ii) optional substituents for alkyl, alkenyl and alkynyl groups comprise one or more members selected from halogen; nitro; cyano; aryl; $CO_2R^{21}$, $NHCOR^{21}$, or $NHCH_2CO_2R^{21}$ wherein $R^{21}$ is hydrogen, $C_1$-$C_6$ alkyl or an agriculturally acceptable cation; $C_1$-$C_6$ alkoxy; oxo; $S(O)_mR^x$ wherein m is 0-, 1, or 2 and $R^x$ is $C_1$-$C_6$ alkyl; amino; mono- or di- ($C_1$-$C_6$) alkylamino; or $CONR^{22}R^{23}$ wherein $R^{22}$ and $R^{23}$ are independently hydrogen, $C_1$-$C_6$ alkyl, $C_2$-$C_6$ alkenyl or $C_2$-$C_6$ alkynyl; and (iii) agriculturally acceptable cations are selected from sodium, potassium or calcium ions; sulphonium or sulphoxonium ions having the formula $S(O)_pR^{14}R^{15}R^{16}$ wherein p is 0 or 1 and $R^{14}$, $R^{15}$ and $R^{16}$ are as defined above; ammonium; and tertiary ammonium ions having the formula $N^+R^{14}R^{15}R^{16}R^{18}$ wherein $R^{14}$, $R^{15}$ and $R^{16}$ are as defined above and $R^{18}$ is as defined above for $R^{14}$.

2. A compound according to claim 1 wherein —A—B— is

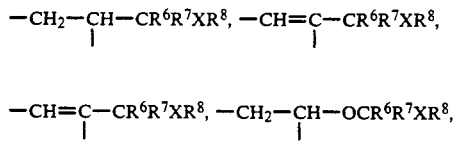

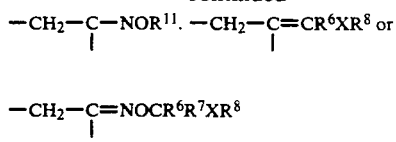

wherein $R^6$, $R^7$, $R^8$, $R^{11}$ and X are as defined in claim 1.

3. A compound according to claim 1 or claim 2 wherein $R^8$ is $CO_2R^{12}$ or $CONR^{14}R^{15}$ wherein $R^{12}$, $R^{14}$ and $R^{15}$ are as defined in claim 1.

4. A compound according to claim 3 wherein $R^{12}$ is $C^{1-6}$ alkyl and $R^{14}$ and $R^{15}$ are independently selected from hydrogen or $C_1$-$C_3$ alkyl.

5. A compound according to claim 1 wherein —A—B is —$CH_2CH$—$CR^6R^7XR^8$ where $R^6$ and $R^7$ are hydrogen and $R^8$ is $CO_2R^{12}$ where $R^{12}$ is $C_{1-6}$ alkyl.

6. A compound according to any one of the preceding claims wherein Ar is a group of sub-formula (i):

where $R^{24}$ is hydrogen or halo; and J is $CR^{25}$ where $R^{25}$ is hydrogen or halo.

7. A herbicidal composition comprising a compound of formula (I) as defined in claim 1 in combination with a carrier or diluent.

8. A method of kiling or controlling the growth of unwanted plants which method comprises applying to the plants or to a locus thereof an effective amount of a compound of formula (I) as defined in claim 1.

* * * * *